United States Patent [19]

Trawöger

[11] Patent Number: 4,534,759
[45] Date of Patent: Aug. 13, 1985

[54] VALVE FOR SUPPLYING, CONTROLLING AND TAKING OUT A MEDIUM CONTAINED IN AN IMPLANTED CONTAINER

[76] Inventor: Werner Trawöger, Höttinger Au Nr. 60, A-6020 Innsbruck, Austria

[21] Appl. No.: 488,543

[22] PCT Filed: Apr. 19, 1982

[86] PCT No.: PCT/AT82/00011
§ 371 Date: Mar. 7, 1983
§ 102(e) Date: Mar. 7, 1983

[87] PCT Pub. No.: WO83/00367
PCT Pub. Date: Feb. 3, 1983

[30] Foreign Application Priority Data

Jul. 16, 1981 [AT] Austria ................................ 3137/81

[51] Int. Cl.³ ............................................. A61B 17/34
[52] U.S. Cl. .................................. 604/117; 604/181; 604/245; 604/256; 251/354
[58] Field of Search ................. 604/93, 181, 117, 183, 604/187, 245–249, 256–257; 251/DIG. 1, 128, 291, 337, 349, 350, 354; 137/539

[56] References Cited

U.S. PATENT DOCUMENTS

| 1,759,798 | 5/1930 | Murphy et al. | 251/128 |
| 3,720,220 | 3/1973 | McMath | 137/539 |
| 3,734,115 | 5/1973 | McMath | 137/539 |
| 4,181,132 | 1/1980 | Parks | 128/399 |
| 4,233,982 | 11/1980 | Bauer et al. | 604/256 |
| 4,256,102 | 3/1981 | Monaco | 604/256 |
| 4,332,255 | 6/1982 | Hakim et al. | 604/247 |

FOREIGN PATENT DOCUMENTS

| 1650538 | 4/1971 | Fed. Rep. of Germany . | |
| 2147957 | 5/1973 | Fed. Rep. of Germany | 251/354 |
| 345438 | 9/1978 | Fed. Rep. of Germany . | |
| 852330 | 1/1940 | France | 137/539 |
| 1327106 | 4/1963 | France . | |
| 2267801 | 11/1975 | France | 604/249 |
| 539163 | 2/1956 | Italy | 251/354 |
| 657136 | 10/1963 | Italy | 251/291 |
| 1441663 | 7/1976 | United Kingdom | 604/256 |

Primary Examiner—C. Fred Rosenbaum
Assistant Examiner—Gene B. Kartchner
Attorney, Agent, or Firm—McGlew and Tuttle

[57] ABSTRACT

For the supply, control or taking of a medium contained in an implanted container the valve has a valve body (2) in which the flow channel (3) is formed by two pocket bores running into each other at an angle. The first pocket bore serves as an introduction channel (5) for the injection needle (15) and is outwardly provided with a conical widening (4). Into the second pocket bore (6) a particularly spherical closure member (7) is inserted which projects into the introduction channel (5) in the closed condition and whose part protruding into a chamber (11) connected with the container is acted upon by an elastic element (9). Preferably an O-ring sunk into an annular groove of the second pocket bore (6) serves as valve seat (8) for the closure member (7).

9 Claims, 2 Drawing Figures

VALVE FOR SUPPLYING, CONTROLLING AND TAKING OUT A MEDIUM CONTAINED IN AN IMPLANTED CONTAINER

The invention relates to a valve for supplying, controlling and taking out a medium contained in an implanted container, comprising a valve body wherein a flow channel is provided which widens conically towards the outer side for the introduction of an injection needle and runs into a chamber connected with the container, and in which a closure member acted upon by a reset means is inserted which clears the flow channel when the injection needle is inserted and recloses it when it is taken out.

DESCRIPTION OF THE KNOWN STATE OF THE ART

A valve of this kind has, for example, become known from the Austrian Patent Specification No. 345.438, which describes an implantable container for the long-term administering of medicaments or the like. The valve is a spring valve and as a component part of the container inserted into a bore conically widening towards the outer side. For filling the implanted container the valve is opened when an injection needle is introduced and automatically closed when it is taken out again. As the straight bore extending through the valve housing has to receive not only the closure member but also the reset spring and both members must remain in the bore when the injection needle is introduced, it has proved that the function of the valve does not fulfil the requirements over long periods of time.

It is, therefore, the object of the invention to provide a valve of this kind which is easy to manufacture and whose service life is substantially longer, in which insertion of the injection needle is not impeded by valve members so that no malfunctions occur even after frequent use, as repairs and replacement of the implant should be excluded as far as possible in order to avoid any unnecessary inconvenience to the patients. The valve to be provided in such manner shall, further, not only be an integral component of an implanted container but, in a different design, be insertable into the body as an individual structural member and connectable to the implanted container by means of a pipe.

DESCRIPTION OF THE CHARACTER OF THE INVENTION

According to the invention this problem is solved such that the flow channel comprises an introduction channel for the injection needle in the form of a first pocket bore and a second pocket bore angularly arranged thereto and leading into the introduction channel, which second pocket bore receives the closure member, whereby the closure member projects into the insertion channel in the closed condition.

In the valve according to the invention the flow channel extends to form a corner, whereby the closure member is laterally pressed away by the inserted injection needle and, hence, lifted from the valve seat. Therefore, the reset means is not arranged in the introduction channel and does not impede the insertion of the injection needle, which is inevitable in the long run, when a spring is introduced into the introduction channel.

Even frequent use of the valve does not result in malfunctions caused by the insertion of the injection needle.

In a first embodiment it is provided that the closure member is a solid of revolution whose diameter is smaller than the diameter of the second pocket bore and that the second pocket bore tapers towards the introduction channel, of first pocket bore whereby an O-ring is provided as valve seat which projects radially inwardly from an annular groove of the second pocket bore.

The closure member, which is particularly of spherical shape, projects in a further embodiment preferably from the second pocket bore into the chamber connected with the container, whereby the projecting part is acted upon by an elastic element. The elastic element is preferably a ring, and the valve body is cylindrical at least in the region of the second pocket bore, whereby the ring surrounds the valve body in the cylindrical region and presses on the projecting part of the closure member.

DESCRIPTION OF THE FIGURES OF THE DRAWING

In the following the invention will now be described in more detail in a preferred embodiment by means of the figures of the attached drawings without being limited thereto.

DESCRIPTION OF A PREFERRED EMBODIMENT

Figure 1:
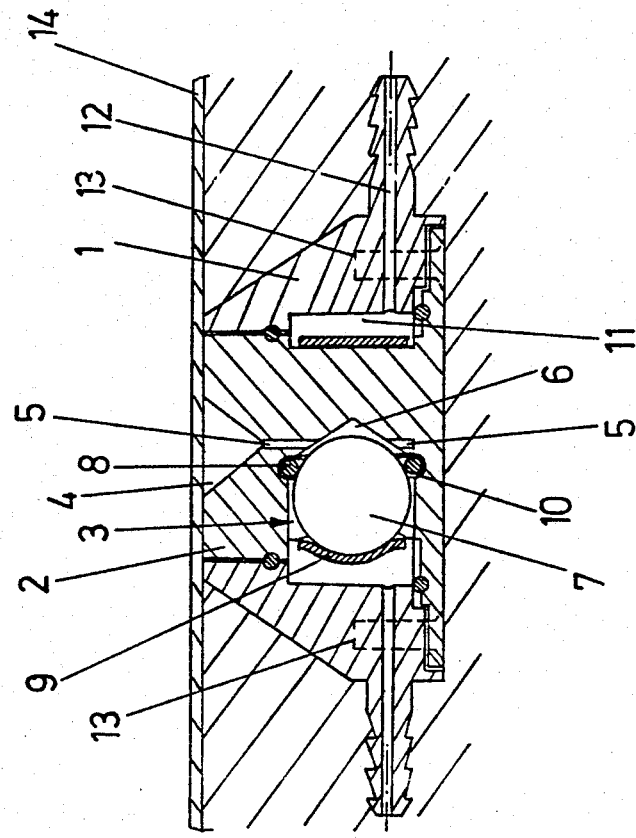
FIG. 1 shows a section through a valve implanted as an individual structural member in the closed position.
Figure 2:
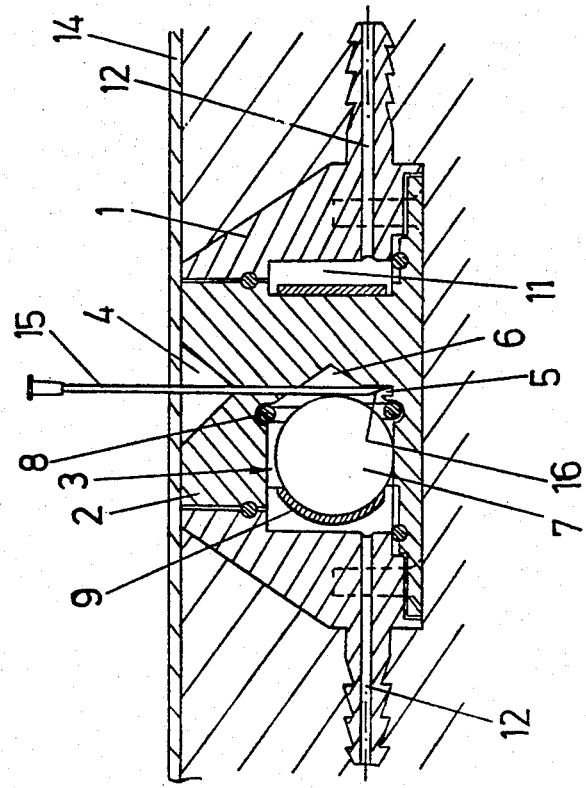
FIG. 2 shows the same in the open position with the injection needle being inserted.

The valve according to the invention comprises a valve body 2, which is in the illustrated embodiment arranged in an implanted valve housing 1. The valve housing 1 could also form the implanted reservoir or container so that the valve body 2 is positioned directly in the container. The valve body 2 is substantially cylindrical and has an annular base plate of greater diameter which is connectable with the valve housing 1 or the container by means of screws 13. The valve housing 1 is provided with a cylindrical bore which widens to an annular chamber 11 from which at least one radial bore 12 leads outwardly through a pipe connector moulded thereto, a connecting pipe to the implanted container being connectable thereto. In the illustrated embodiment two pipe connectors of this kind are provided. A valve of this kind can, therefore, be inserted into a pipe implanted in the body which extends, for example, between an externally compressible reservoir and a pressure collar which surrounds a tubeshaped organ of the body to change its cross-section. The valve body 2 has an axially extending first pocket bore of first blind bore which represents an introduction channel 5 for an injection needle 15 (FIG. 2) to be inserted and has a conical widening 4 towards the skin 14 in order to facilitate the insertion of the needle into the introduction channel 5 when piercing the skin 14. The introductory channel or first blind bore 5 terminates inwardly at a flow channel limiting end portion in the chamber 11. A second pocket bore or second pocket bore 6 leads radially into the introduction channel 5 and receives a closure member 7 having a spherical shape. The second pocket bore 6 thus intersects the first pocket bore 5 at an angle, e.g.

perpendicularly, thereto (cf. FIG. 1). The diameter of the closure member 7 is slightly smaller than the diameter of the pocket bore 6 so that a flow channel 3 remains free. An O-ring serves as a valve seat 8 which is inserted into an annular groove 10 of the pocket bore 6 and projects inwardly. The closure member 7 extends with its innermost region into the introduction channel 5, whereas its outermost region projects from the pocket bore 6 into the chamber 11. An elastic ring 9 serves as a reset means which surrounds the cylindrical valve body 2 in the region of the pocket bore 6 and rests against the projecting region of the closure member 7. For fixing the ring 9 to the valve body 2, the latter is in this region provided with an annular groove. In the closed condition according to FIG. 1 the closure member 7 is pressed against the valve seat 8 by means of the ring 9. When, according to FIG. 2, an injection needle is inserted into the introduction channel 5 the part of the closure member 7 projecting into the introduction channel 5 is displaced, and the closure member is lifted from the valve seat 8, thereby being pressed against the lower wall region of the pocket bore 6 through the motion of the injection needle 15. The liquid to be supplied now exists from the outlet 16 of the injection needle 15 and enters through the cleared flow channel 3 into the chamber 11 from which it can flow through the bores 12 into an attached tube. When the injection needle 15 has been taken out, the elastic ring 9 presses the closure member 7 further into the valve seat 8, thus closing the valve.

Instead of refilling, liquid can obviously also be taken out in the same manner or its pressure can be controlled if a manometer is connected with the injection needle 15. If the valve is implanted directly under the skin 14 as an individual structural member in a separate valve housing 1 its surface is preferably provided with easily tangible depressions so that the injection needle 15 can without difficulties be stuck into the introduction channel 5 having the widening 4 immediately under the skin 14.

The surface of the valve body 2 directed towards the skin 14 in which the widening 4 is disposed can, if desired, be provided with a thin silicone skin, for example, which also covers the widening 4 and is pierced by the injection needle. By such coating a closure of the widening and, maybe, of the opening of the introduction channel 5 by the skin 14, which might be possible, can be obviated.

I claim:

1. Valve for supplying, controlling and taking out a medium contained in an implanted container, comprising a valve body having an exterior and an interior, wherein a flow channel is provided which widens conically toward the exterior of said valve body for the introduction of an injection needle and which runs into a chamber in the interior of the valve body, said chamber being connectable with said container, and in which chamber a closure member acted upon by a reset means is inserted which clears said flow channel when said injection needle is inserted and recloses when it is taken out, characterized in that said flow channel (3) comprises an introduction channel (5) for said injection needle (15) in the form of a first pocket bore terminating at a needle penetration limiting end portion in said chamber and a second pocket bore (6) angularly arranged crosswise relative to and intersecting said introduction channel (5), which said second pocket bore receives said closure member (7), whereby said closure member (7) projects into said introduction channel (5) in the closed condition.

2. Valve of claim 1 wherein the angularly arranged second pocket bore (6) extends radially from said introduction channel (5).

3. Valve of claim 1 wherein the closure member (7) is a solid of revolution whose diameter is smaller than the diameter of said second pocket bore (6) and said second pocket bore (6) inwardly tapers towards the introduction channel (5), whereby an O-ring is provided as a valve seat (8) which projects radially inwardly from an annular groove (10) of said second pocket bore (6).

4. Valve of claim 1 wherein the closure member (7) also projects from said second pocket bore (6) into said chamber (11) and the so projecting part is acted upon by an elastic element.

5. Valve of claim 4 wherein said valve body (2) is cylindrical at least in the region of said second pocket bore (6) and is surrounded by an elastic ring (9) which acts upon said so projecting part of said closure member (7).

6. Valve of claim 5 wherein said closure member (7) is in the form of a ball.

7. Valve of claim 1 wherein such valve is arranged in a subcutaneously implantable valve housing (1) having a pipe connector (12), connectable with the implanted container.

8. Valve for supplying, controlling and taking out a medium contained in an implanted container, comprising a valve body having a chamber connectable with said container, a flow channel leading from said chamber to the exterior of said valve body for the introduction of an injection needle, said flow channel including an introduction channel for said injection needle in the form of a first blind bore terminating at a needle penetration limiting end portion and a second blind bore arranged crosswise to and intersecting said first blind bore, a closure member acted upon by a reset means being received in said second blind bore and projecting into said first blind bore in the closed condition of the valve under the action of said reset means acting in the crosswise direction of said second blind bore relative to said first blind bore and which closure member clears said flow channel when said injection needle is inserted to displace said closure member against the action of said reset means to the open condition of said valve.

9. Valve of claim 8 wherein said closure member is in the form of a ball and said reset means is an elastic element.

* * * * *